US007464588B2

(12) United States Patent
Steinsiek

(10) Patent No.: US 7,464,588 B2
(45) Date of Patent: Dec. 16, 2008

(54) APPARATUS AND METHOD FOR DETECTING FLUID ENTERING A WELLBORE

(75) Inventor: Roger Steinsiek, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 0 days.

(21) Appl. No.: 11/250,598

(22) Filed: Oct. 14, 2005

(65) Prior Publication Data

US 2007/0084277 A1    Apr. 19, 2007

(51) Int. Cl.
*E21B 47/08* (2006.01)
(52) U.S. Cl. .................................... 73/152.55
(58) Field of Classification Search .............. 73/152.55, 73/152.58, 152.32, 64.53
See application file for complete search history.

(56) References Cited

U.S. PATENT DOCUMENTS

| 2,573,390 | A | * | 10/1951 | Blanchard | 340/606 |
|---|---|---|---|---|---|
| 3,427,481 | A | * | 2/1969 | Colbert et al. | 310/327 |
| 3,603,145 | A | * | 9/1971 | Morris | 73/152.32 |
| 3,908,454 | A | | 9/1975 | Mullins et al. | |
| 4,015,194 | A | * | 3/1977 | Epling | 324/324 |
| 4,092,628 | A | | 5/1978 | Hall, Jr. | |
| 4,208,906 | A | * | 6/1980 | Roberts, Jr. | 73/152.32 |
| 4,273,212 | A | * | 6/1981 | Dorr et al. | 181/102 |
| 4,492,865 | A | * | 1/1985 | Murphy et al. | 250/265 |
| 4,596,143 | A | | 6/1986 | Norel | |
| 4,599,713 | A | | 7/1986 | Rudaz et al. | |
| 4,733,232 | A | * | 3/1988 | Grosso | 367/82 |
| 4,754,839 | A | * | 7/1988 | Gold et al. | 181/102 |
| 5,130,950 | A | * | 7/1992 | Orban et al. | 367/34 |
| 5,275,040 | A | * | 1/1994 | Codazzi | 73/152.22 |
| 5,301,170 | A | | 4/1994 | James | |

(Continued)

FOREIGN PATENT DOCUMENTS

EP    1426788    6/2004

(Continued)

OTHER PUBLICATIONS

Compact Ultrasonic Gas Detector-MGD & MHT.

(Continued)

*Primary Examiner*—Hezron Williams
*Assistant Examiner*—John Fitzgerald
(74) *Attorney, Agent, or Firm*—Madan Mossman & Sriram PC

(57) ABSTRACT

The method and apparatus of the present invention provides for detecting a flow of a formation fluid entering into a wellbore. An ultrasonic sensor is placed in a wellbore. The sensor has a resonant member that is exposed to a fluid in the wellbore. At a location in the wellbore, acoustic energy is measured wherein the acoustic energy is related to turbulence from formation fluid entering the wellbore. In another embodiment of the invention a tool is provided for detecting a flow of a formation fluid into a downhole location in a wellbore. The ultrasonic sensor has a resonant member that is adapted to be in contact with a fluid in the wellbore. The sensor generates electrical signals when exposed to ultrasonic turbulences caused by a formation fluid entering into the wellbore. A processor processes the electrical signals to detect the flow of the formation fluid entering into the wellbore.

20 Claims, 4 Drawing Sheets

U.S. PATENT DOCUMENTS

| | | | |
|---|---|---|---|
| 5,351,532 A * | 10/1994 | Hager | 73/152.55 |
| 5,470,216 A | 11/1995 | Saito et al. | |
| 5,561,245 A * | 10/1996 | Georgi et al. | 73/152.02 |
| 5,592,438 A * | 1/1997 | Rorden et al. | 367/83 |
| 5,635,685 A | 6/1997 | Tierce et al. | |
| 5,644,186 A | 7/1997 | Birchak et al. | |
| 5,668,303 A * | 9/1997 | Giesler et al. | 73/24.06 |
| 5,731,550 A | 3/1998 | Lester et al. | |
| 5,736,637 A * | 4/1998 | Evans et al. | 73/152.31 |
| 5,850,369 A * | 12/1998 | Rorden et al. | 367/83 |
| 5,866,815 A | 2/1999 | Schwald et al. | |
| 5,987,385 A | 11/1999 | Varsamis et al. | |
| 6,058,786 A * | 5/2000 | Wallen et al. | 73/861.28 |
| 6,135,234 A | 10/2000 | Harris et al. | |
| 6,208,586 B1 * | 3/2001 | Rorden et al. | 367/35 |
| 6,354,146 B1 | 3/2002 | Birchak et al. | |
| 6,466,513 B1 | 10/2002 | Pabon et al. | |
| 6,488,116 B2 | 12/2002 | Bailey | |
| 6,648,083 B2 * | 11/2003 | Evans et al. | 175/41 |
| 6,768,106 B2 * | 7/2004 | Gzara et al. | 250/269.3 |
| 6,895,825 B1 * | 5/2005 | Barkhoudarian | 73/861.28 |
| 6,938,470 B2 * | 9/2005 | DiFoggio et al. | 73/152.24 |
| 7,036,363 B2 * | 5/2006 | Yogeswaren | 73/152.16 |
| 2005/0000279 A1 * | 1/2005 | Yogeswaren | 73/152.58 |
| 2006/0101916 A1 * | 5/2006 | Griffiths et al. | 73/597 |

FOREIGN PATENT DOCUMENTS

| | | |
|---|---|---|
| WO | WO 99/45235 | 9/1999 |
| WO | WO2004/111388 | 12/2004 |

OTHER PUBLICATIONS

TecWel, Digital Singal Processing Well Logging Tool; TecWel; Well Leak Detector (WLD).

Flexural-extensional behavior of composite piezoelectric circular plates; N. T. Adelman and Y. Stavsky; Department of Aeronautical Engineering Technion, Israel Institute of Technology, Haifa, Israel (Received Aug. 28, 1978, accepted for publication Aug. 10, 1979).

Calculation of the characteristics of a membrane-type flexural-mode piezoelectric transducer; Yu. T. Antonyak and M. E. Vassergiser; All-Union Scientific-Research Institute of Measurement and Control System Metrology; Sumitted May 5, 1980; resubmitted May 4, 1981.

* cited by examiner

APPARATUS AND METHOD FOR DETECTING FLUID ENTERING A WELLBORE

FIELD OF THE INVENTION

The invention relates generally to the field of the evaluation for hydrocarbons in a wellbore, and more specifically to a method and apparatus for detecting flow of formation fluids into wellbores.

BACKGROUND OF THE INVENTION

Downhole tools, such as wireline tools, bottom hole assemblies attached to a drill string, each having a variety of sensors are commonly utilized to determine a variety of parameters of interest relating the subsurface formations, including detection of formation fluids flowing into the wellbores. It is useful to detect the presence, extent, and location (depth) of the wellbore fluids entering a wellbore. Such information may be utilized for completing the wells, performing remedial work and/or to determine one or more characteristics of the reservoir or the formation.

An increase in the demand of natural gas has led to the need to complete low volume gas wells. This demand has caused the oil and gas exploration industry to identify small, low volume gas entering into the wellbores. These wells may be air drilled boreholes or drilled utilizing drilling fluid. It is thus useful to detect the presence and location of such small gas producing zones.

Also, of importance is the detection of liquids into the wellbores whether prior to completing such wells for producing hydrocarbons or after completion. It is useful to detect whether a formation fluid is leaking into a wellbore after completion for remedial work. Acoustic sensors, including ultrasonic sensors, carried by downhole tools have been utilized to detect formation fluid flows into the wellbores. In certain downhole situations, fluid entering the wellbores through small areas create turbulences in the wellbore fluid (which may be liquid or air) in the ultrasound frequency range. Ultrasonic sensors have been utilized to detect such turbulence. Ultrasonic sensors utilizing a piezoelectric element have been utilized. Such sensors are enclosed in an outer casing which may be a metallic or a non-metallic (plastic, rubber, etc.) housing to protect the sensor from the borehole environment (high pressure and temperature). The protective encasement tends to reduce the ability of the sensor to detect the ultrasonic turbulence due to the sound reflection and/or attenuation due to the protective casing material.

Thus, it is desirable to have downhole tools that include ultrasonic sensors that have greater sensitivity and which are able to withstand the downhole environment, i.e., high temperatures and high pressures (which may be greater that 300 degrees Fahrenheit and over 20,000 psi). The present invention provides an apparatus and method that address the above-noted problems.

SUMMARY OF THE INVENTION

One aspect of the invention provides a method of detecting a flow of a formation fluid entering into a wellbore. An ultrasonic sensor is placed in a wellbore. The sensor has a resonant member that is exposed to a fluid in the wellbore. The sensor is tuned to a resonant frequency and is pressure and temperature balanced for use in wellbore. Acoustic energy relating to turbulence from formation fluid entering the wellbore is measured utilizing the ultrasonic sensor. Signals from the sensor are processed to determine the presence of the formation fluid entering into the wellbore and correlated with the location (depth) in the wellbore utilizing the sensor depth data obtained from the depth measurements made relating to the sensor location in the wellbore. The method also provides utilizing a set of sensors arranged circumferentially a tool to obtain full coverage of measurements along the inner circumference of the wellbore. The method further provides for utilizing an additional set of sensors longitudinally spaced from the first set to correlate data to accurately determine the presence and location of the entry of the fluid into the wellbore.

In another embodiment of the invention a tool is provided for detecting a flow of a formation fluid at a downhole location in a wellbore. The tool includes at least one ultrasonic sensor. The ultrasonic sensor has a resonant member that is adapted to be in direct contact with the wellbore fluid. The ultrasonic sensor is tuned to a resonant frequency and generates electrical signals when exposed to ultrasonic turbulences caused by the formation fluid entering into the wellbore. A processor processes the electrical signals to detect the flow of the formation fluid entering into the wellbore. A temperature sensor carried by the tool measures the temperature of the wellbore fluid and the processor correlates the information from the temperature and the ultrasonic sensor to verify the detection of the formation fluid entering the wellbore.

The method and apparatus of the invention provides embodiments of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

BRIEF DESCRIPTION OF THE FIGURES

The present invention and its advantages will be better understood by referring to the following detailed description and the attached drawings in which.

While the invention will be described in connection with its preferred embodiments, it will be understood that the invention is not limited thereto. It is intended to cover all alternatives, modifications, and equivalents which may be included within the spirit and scope of the invention, as defined by the appended claims.

DETAILED DESCRIPTION OF THE INVENTION

In view of the above, the present invention through one or more of its various aspects and/or embodiments is described to provide one or more advantages, such as noted below.

Figure 1:
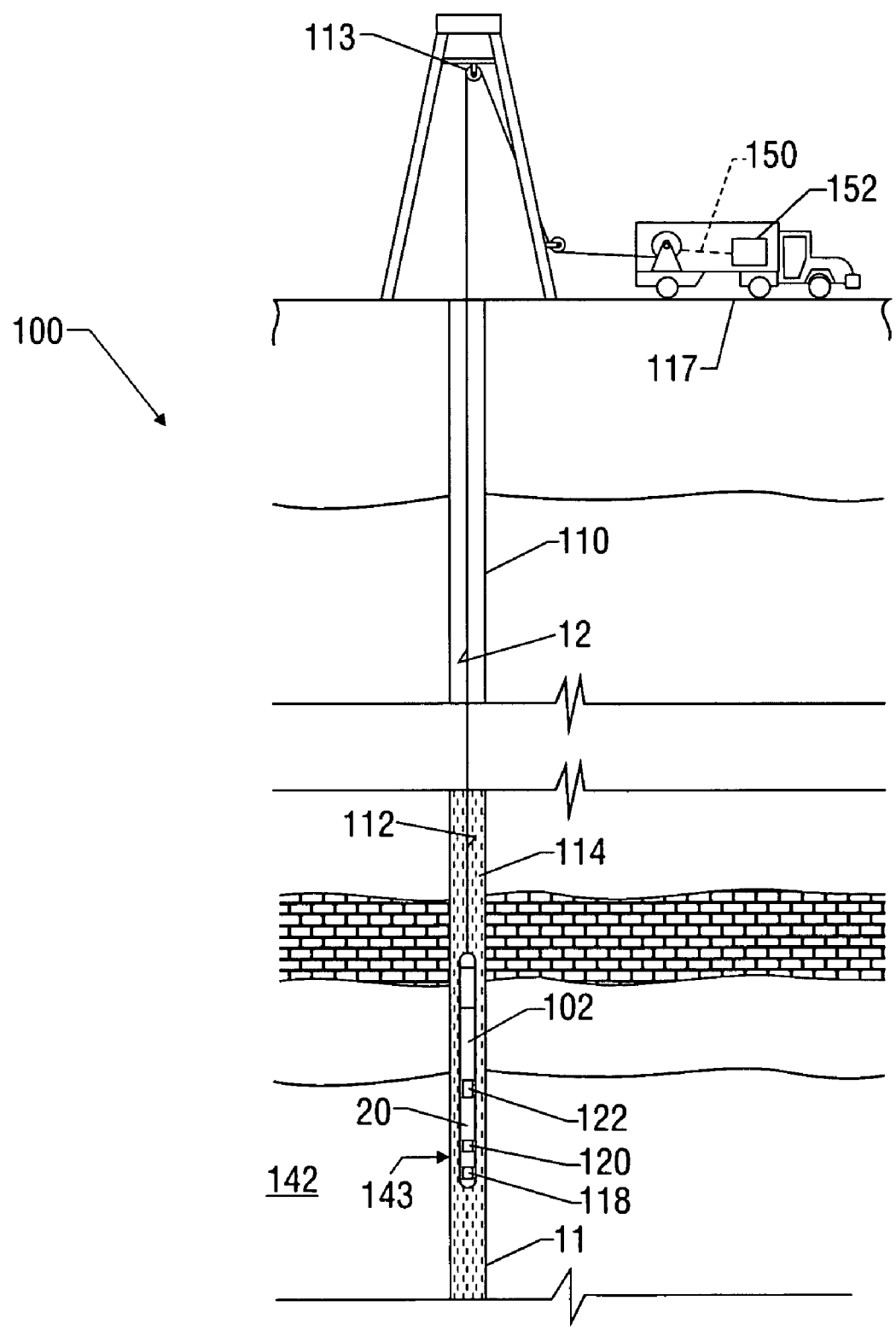
FIG. 1 illustrates a downhole tool for detecting fluids entering into a wellbore according to one exemplary embodiment of the present invention.

FIG. 1 illustrates a system 100 for detecting fluid flow into a wellbore. The system 100 shows a downhole tool 100 placed in a wellbore 110 utilizing a tool carrying member 112, which may be a wireline, tubing, slick line or any other suitable carrying member. The wellbore 110 may contain air or a liquid, such as a drilling fluid or production fluid, as a medium 118. The tool 102 is shown to include a lower acoustic sensor arrangement or set 120 and an upper acoustic sensor arrangement or set longitudinally spaced apart from the lower sensor set by a known distance. Each sensor arrangement may include multiple ultrasonic sensors, each such sensor further may be an ultrasonic sensor. The sensors in each sensor arrangement may be placed circumferentially around the tool 102 to provide a full coverage of measurements around the borehole 110. In one aspect, the individual sensors each may provide a limited circumferential coverage. In such a case, several circumferentially spaced sensors, for example six or seven, may be utilized as sensor sets to provide the full coverage. The structure and operation of each such sensor and the sensor sets is described in more detail below. The tool 102 further may contain a temperature sensor 130 that measures the temperature of the wellbore medium 118. The tool 102 is shown lowered into the wellbore via a pully by a wireline 112 on a winch 117 placed on suitable carrier, such as a truck 115 (for land operations) or an offshore platform (for offshore operations). A computer system 150, that may include a processor 152 is coupled to the tool 102 via power and data lines carried by the conveying member 112. The computer system 150 contains one or more memory storage devices, visual displays, other equipment, and computer programs embedded on one or more computer readable media that is accessible to the computers for performing the methods, operations and the functions relating to the tool 102 according to the present invention.

Still referring to FIG. 1, a formation fluid 142 entering the wellbore at a location 143, in some instances, may cause or create turbulence in the wellbore 110 in the ultrasonic frequency range. The sensors in each sensor set 120 and 122, in one aspect, are tuned to a suitable frequency to detect acoustic frequencies in the ultrasonic range. In one aspect, each individual sensor is tuned to approximately 40 KHz, although any other frequency may be utilized. As the tool 102 is moved in the wellbore 110, for example, toward the surface, individual sensors in sensor set 120 and 122 detect turbulence created by the fluid 142 in the ultrasonic range, each sensor providing corresponding electrical responses or signals. The signals from each such sensor or from multiple sensors in a set combined with each other may be processed to detect or determine the presence of the fluid 142 entering the wellbore 110. Similarly, the sensor set 120 provides signals responsive to the turbulence when the sensors in the set 120 are proximate to the fluid entry location 143. The data from the two sensor sets 120 and 122 may be correlated to provide an accurate detection and determination of the location or depth of the fluid entry location 143. The processor 152 may be disposed in the tool 102 or at the surface 115 or it may be distributed.

Figure 2:
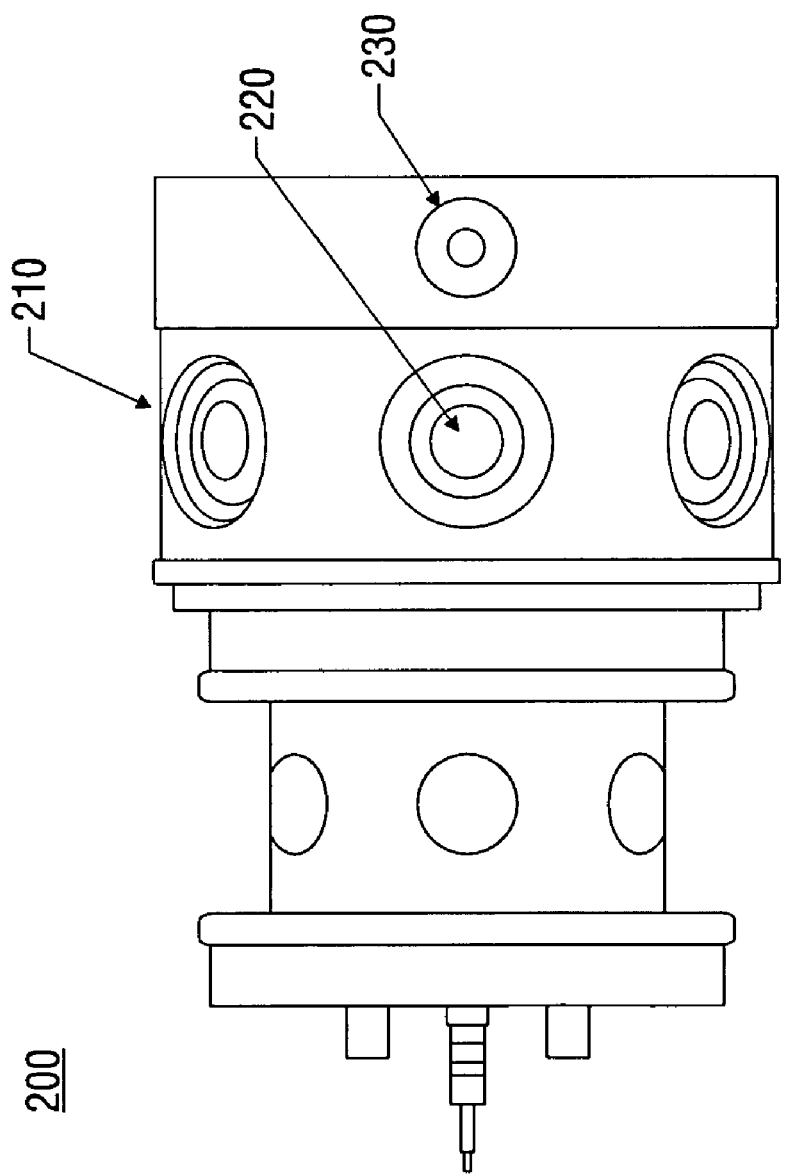
FIG. 2 illustrates a section of a downhole tool for detecting acoustic energy in a wellbore.

FIG. 2 illustrates a section 200 of a downhole tool for detecting acoustic energy in a borehole. The section may be located in the upper or lower portion of downhole tool 102. This section of the tool 102 contains circumferentially arranged portals 210 for housing ultrasonic sensors 220 within the portals. A separate portal is provided for each sensor of a sensor set. The section 200 also includes a liquid fill opening 230. Enough portals may be provided so that full acoustic coverage of an inside circumference of the wellbore is enabled as discussed above with reference to FIG. 1. In one embodiment, two sets of sensors, each set with seven portals with seven sensors may be used in a downhole tool, one set located in an upper tubular tool section and another at a lower tubular tool section.

Figure 3:
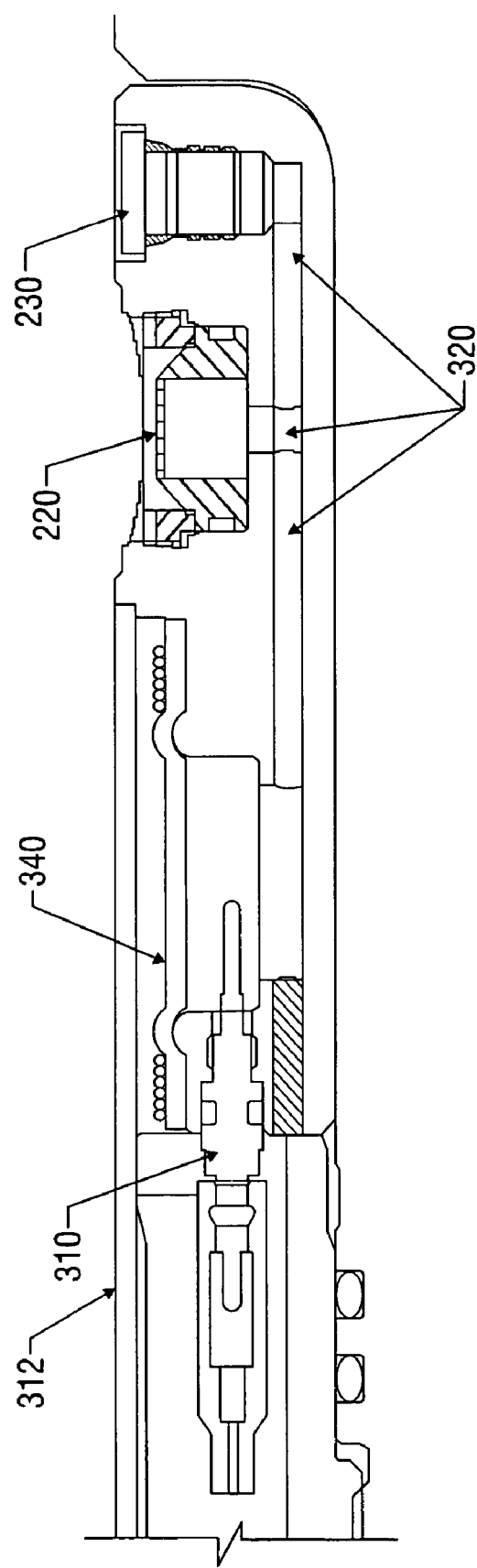
FIG. 3 illustrates a cross-section of a section of a downhole tool that shows a sensor and pressure compensation system in a tool body according to an exemplary embodiment of the present invention.
Figure 4:
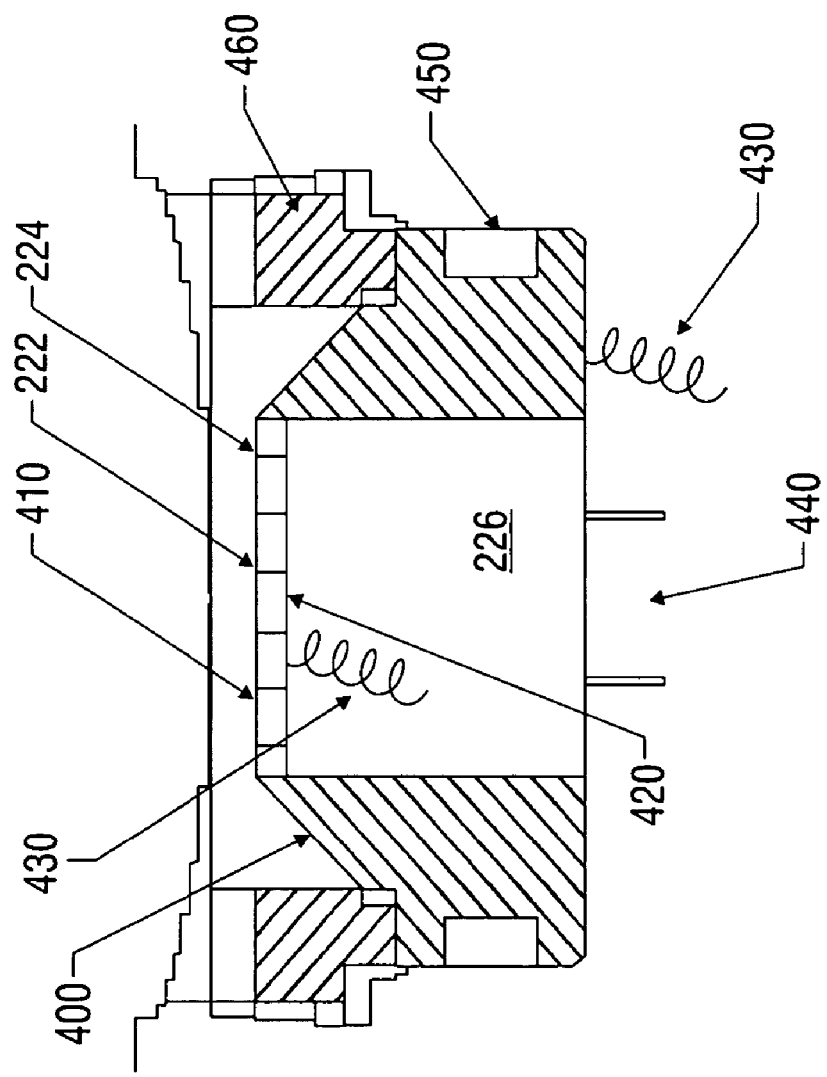
FIG. 4 illustrates a cross-section of an acoustic sensor made according to an exemplary embodiment of the present invention.

FIG. 3 illustrates a cross-section of the tool section illustrated in FIG. 2. Each ultrasonic sensor 220 is securely placed in its corresponding portal within the tool housing 312. Referring also to FIG. 4, which is an illustration of sensor 220, an outer surface 222 of a resonant member 224 of the sensor 220 is directly exposed to the environment outside of the tool during operation, i.e., when the tool is in the wellbore, the surface 222 is exposed to wellbore fluid. The housing 312 includes a conduit or fluid line 320 to provide fluid communication between a sensor cavity 226 and a flexible member 340. The conduit 320 and the flexible member 340 provide pressure compensation for the oil to expand or contract when the tool is downhole. The oil provides for both temperature and pressure compensation as borehole conditions change. The fluid line 320 and the sensor cavity 226 are filled with a suitable light viscosity oil, such as silicone having a density of less than 100 centistokes. Any other suitable liquid may also be utilized for the purpose of this invention.

FIG. 4 illustrates a cross section of an acoustic sensor 220 provided according to one embodiment of the invention. As noted above, sensor 220 may be located within one of several portals around the downhole tool 102. A housing 400, which may be made of tungsten, contains a membrane member 410, which has an outer surface 222 that is exposed to the outside environment. The inner surface of the membrane is attached to a piezoelectric member 420, which may be a plate, by a suitable resin or by any other suitable material or technique. The membrane 410 with the piezoelectric member 420 together form the resonant member 224 of the sensor 220. Electrodes 430 may be attached to the piezoelectric plate 420 and to the sensor housing 400. An opening 440 to the cavity 226 enables the fluid flow between the sensor and the flexible member via the fluid line 320 to compensate for the pressure variations as the oil expands or contracts in the wellbore. The housing 400 may have sealing materials 450 and fastening apparatus 460.

The resonant member 224 of sensor 220 may be tuned to be more or less sensitive to different ranges by varying the diameter and thickness of the membrane member 410 as well as the piezoelectric plate 420. These tuning methods are well understood by practitioners in the art. For example, frequency ranges around 40 kilohertz are useful for the detection of hydrocarbon fluid flow. A membrane member 410 of thickness of about 0.020 inches with an appropriately adjusted piezoelectric plate 420 may be used to form a sensor's resonant member that may provide adequate sensitivity in the acoustic frequency ranges useful for hydrocarbon fluid flow detection. The sensor 220 may also be tuned to any desired frequency in-situ utilizing electrical circuits. The sensor may be tuned to any desired frequency within a range of frequencies. A feedback circuit may be provided that determines the desired frequency and a processor tunes the sensor to that desired frequency. This method allows for adjusting the resonant frequency as the downhole conditions change. The exemplary, non-limiting, sensor 220 described herein is shown to include a singe resonant member directly exposed to the wellbore fluid, which sensor is tuned to a selected frequency in a range of frequencies, and which is further pressure compensated by a liquid medium inside the sensor. Single membrane acoustic sensors sometimes are referred in the art as unimorph mode or flexural mode tranducers. Other sensors, including but not limited to sensors having piezoelectric elements with impedance matching and directly in contact with the wellbore fluid may also be utilized. Such sensors are referred to as extensional mode or radial mode tranducers.

Thus, the present invention provides a method, apparatus and system for determining flow of a formation fluid entering into a wellbore. In one non-limiting embodiment the invention provides a method that includes placing an ultrasonic sensor that has a resonant member exposed to a fluid in the wellbore and measuring, at a depth of the wellbore, acoustic energy related to turbulence caused by the formation fluid entering into the wellbore. A location of the formation fluid entering the wellbore from the detected turbulence is then determined. Temperature may also be measured at the location and the acoustic energy and temperature may be correlated to verify the location of the fluid entering the wellbore. The resonant member of the ultrasonic sensor may be tuned to selected frequency ranges. Tuning may be accomplished by selecting dimensions of the resonant member (the thickness and diameter of the sensor membrane part as well the piezoelectric plate) that defines a selected resonant frequency or the ultrasonic sensor, or the tuning may occur by applying the sensor in-situ to an electric circuit. The tuning may be occur when the downhole tool is located within the wellbore. The resonant member of the ultrasonic sensor may be attached to a housing adapted to contain a liquid and wherein the resonant member further comprises a metallic membrane exposed to an outside environment and a piezoelectric member that is protected from the outside environment. The ultrasonic sensors may be located around a tubular member to provide substantially a full acoustic coverage of an inside circumference of the wellbore. The ultrasonic sensor may be tuned to a frequency of about 40 KHz. Pressure compensation may be provided to the ultrasonic sensor when the ultrasonic sensor is in the wellbore.

In one embodiment, the invention provides an apparatus for detecting flow of a formation fluid into a wellbore at a downhole location. The apparatus comprises at least one ultrasonic sensor carried by the tool, the ultrasonic sensor having a resonant member adapted to be in contact with the borehole fluid. The ultrasonic sensor generates electrical signals when exposed to ultrasonic turbulences caused by a formation fluid entering into the wellbore. A processor may be provided that processes the electrical signals to determine location of the formation fluid entering the wellbore. The resonant member may be attached to a housing that is adapted to contain a liquid therein to provide pressure compensation to the resonant member when the tool is in the wellbore. The resonant member may have a membrane member and a piezoelectric member attached to the membrane. The membrane may be a relatively thin metallic member, such as titanium membrane about 0.020 inches thick. The resonant member membrane may define a resonant frequency of the ultrasonic sensor. A circuit may be utilized to tune the resonant member to a selected resonant frequency. The resonant frequency of the resonant member may be above the audio frequency, such as about 40 KHz. The liquid in the sensor provides pressure compensation and may be made to be in fluid communication with a liquid reservoir or with a flexible member that enables the liquid in the sensor to expand and contract downhole. A plurality of ultrasonic sensors may be arranged around a tubular member of the tool, and these sensors may provide substantially full acoustic measurement coverage of an inside circumference of the wellbore. A temperature sensor may be provided that measures temperature of the fluid in the wellbore and the processor may correlates the measured temperature with the electrical signals to verify the location of the fluid entering into the wellbore.

The embodiments described herein, therefore, are well adapted to carry out the invention. While various embodiments of the invention have been given for purposes of disclosure, numerous changes known to persons of skill in the art may be made to practice the invention and to accomplish the results contemplated herein, without departing from the concept or the spirit of the invention. Various modifications will be apparent to those skilled in the art. It is intended that all such variations that are within the scope and spirit of the appended claims be embraced by the foregoing disclosure.

What is claimed is:

1. A method of detecting flow of a fluid entering from a formation into a wellbore, comprising:
    placing a resonant member of an acoustic sensor in direct fluid communication with the fluid entering the wellbore in the wellbore at a selected depth;
    measuring with the sensor an acoustic energy received directly from the fluid entering from the formation into the wellbore; and
    detecting the flow of the formation fluid entering into the wellbore using the acoustic energy measured by the sensor.

2. The method of claim 1 further comprising: measuring a temperature in the wellbore and correlating the measured temperature and the acoustic energy measured by the sensor to verify the detection of the fluid entering into the wellbore.

3. The method of claim 1 further comprising tuning the resonant member of the acoustic sensor by one of: (i) selecting a dimension of the resonant member that defines, at least in part, a selected resonant frequency of the sensor, and (ii) tuning the sensor to a resonant frequency in-situ utilizing an electric circuit.

4. The method of claim 1 further comprising attaching the resonant member of the acoustic sensor to a housing that is adapted to contain a liquid and wherein the resonant member further comprises a metallic membrane that is in direct contact with the fluid in the wellbore and a piezoelectric member that is protected from the wellbore fluid.

5. The method of claim 1 further comprising placing a plurality of acoustic sensors around a tubular member to provide substantially a full acoustic coverage of an inside circumference of the wellbore.

6. The method of claim 1 further comprising tuning the acoustic sensor to a frequency of about 40 KHz.

7. The method of claim 1, wherein detecting the flow of the formation fluid entering into the wellbore is done by primarily processing signals generated by the sensor in response to the acoustic energy received directly from the fluid entering from the formation into the wellbore.

8. The method of claim 1 further comprising providing pressure compensation for the acoustic sensor for use in the wellbore.

9. The method of claim 8 wherein providing the pressure compensation includes utilizing a liquid in pressure communication between the acoustic sensor and a flexible member.

10. A tool for detecting flow of a fluid entering from a formation into a wellbore ("formation fluid"), comprising:
    at least one acoustic sensor carried by the tool, the at least one acoustic sensor having a resonant member adapted to be in direct contact with the fluid entering into the wellbore, wherein the at least one acoustic sensor is configured to generate electrical signals responsive to acoustic energy generated by the formation fluid while entering into the wellbore; and
    a processor configured to process the electrical signals to detect the flow of the formation fluid entering into the wellbore.

11. The tool of claim 10 wherein the resonant member of the at least one acoustic sensor is attached to a housing that contains a liquid therein to provide pressure compensation to the resonant member when the tool is in the wellbore.

12. The tool of claim 10 wherein a liquid in a housing in pressure communication with the resonant member provides pressure compensation to the acoustic sensor.

13. The tool of claim 10 wherein the at least one acoustic sensor includes a plurality of ultrasonic sensors arranged around a tubular member and configured to provide substantially a full acoustic coverage of an inner circumference of the wellbore.

14. The tool of claim 10 further comprising a temperature sensor configured to measure temperature of the fluid in the wellbore and wherein the processor is configured to correlate data from the measured temperature and the electrical signals to verify the location of the formation fluid entering into the wellbore.

15. The apparatus of claim 10, wherein the processor primarily processes the electrical signals from the acoustic sensor to detect the flow of the formation fluid entering into the wellbore.

16. The tool of claim 10 further comprising a circuit configured to tune the resonant member to a selected resonant frequency.

17. The tool of claim 16 wherein the resonant member has a resonant frequency of about 40 KHz.

18. The tool of claim 10 wherein the at least one acoustic sensor is an ultrasonic sensor and wherein the resonant member comprises:

a membrane; and a piezoelectric member attached to the membrane.

19. The tool of claim 18 wherein the membrane is a metallic membrane having a thickness of about 0.020 inches.

20. The tool of claim 18 wherein dimensions of the membrane define, at least in part, a resonant frequency of the at least one acoustic sensor.

\* \* \* \* \*

UNITED STATES PATENT AND TRADEMARK OFFICE
CERTIFICATE OF CORRECTION

| | | |
|---|---|---|
| PATENT NO. | : 7,464,588 B2 | Page 1 of 1 |
| APPLICATION NO. | : 11/250598 | |
| DATED | : December 16, 2008 | |
| INVENTOR(S) | : Roger Steinsiek | |

It is certified that error appears in the above-identified patent and that said Letters Patent is hereby corrected as shown below:

Column 6, claim 1, line 16, delete "in the wellbore".

Signed and Sealed this

Twenty-third Day of March, 2010

David J. Kappos
*Director of the United States Patent and Trademark Office*